United States Patent
Kreuzberg et al.

(10) Patent No.: US 10,668,198 B2
(45) Date of Patent: Jun. 2, 2020

(54) BLOOD TREATMENT APPARATUS FOR REDUCING THE PROBABILITY OF CONTACT PHASE ACTIVATION

(71) Applicant: FRESENIUS MEDICAL CARE DEUTSCHLAND GMBH, Bad Homburg (DE)

(72) Inventors: Ursula Kreuzberg, Leverkusen (DE); Cacilia Scholz, Schwalbach (DE); Stefano Stuard, Francavilla al Mare (IT); Wolfgang Wehmeyer, Tuebingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 29 days.

(21) Appl. No.: 15/752,132

(22) PCT Filed: Aug. 10, 2016

(86) PCT No.: PCT/EP2016/001382
§ 371 (c)(1),
(2) Date: Feb. 12, 2018

(87) PCT Pub. No.: WO2017/025199
PCT Pub. Date: Feb. 16, 2017

(65) Prior Publication Data
US 2018/0236151 A1 Aug. 23, 2018

(30) Foreign Application Priority Data

Aug. 11, 2015 (DE) .................. 10 2015 010 417

(51) Int. Cl.
*B01D 11/00* (2006.01)
*B01D 61/00* (2006.01)
(Continued)

(52) U.S. Cl.
CPC ........ *A61M 1/1607* (2014.02); *A61M 1/1656* (2013.01); *A61M 1/1666* (2014.02);
(Continued)

(58) Field of Classification Search
USPC ................. 210/85, 96.2, 141, 645, 646, 647
See application file for complete search history.

(56) References Cited

FOREIGN PATENT DOCUMENTS

| DE | 102014113728 | 3/2016 |
|---|---|---|
| EP | 2583700 | 4/2013 |

(Continued)

OTHER PUBLICATIONS

EP2583700A1 Breuch—Method for starting haemodialysis (Abstract & MT; Apr. 24, 2013) (Year: 2013).*
(Continued)

*Primary Examiner* — Hayden Brewster
(74) *Attorney, Agent, or Firm* — Jacobson Holman, PLLC.

(57) ABSTRACT

A blood treatment apparatus having an extracorporeal circuit has a dialyzate circuit with a dialyzer, having a blood-side chamber, and a dialyzate-side chamber separated from the blood-side chamber by a membrane. The blood-side chamber is in fluid communication with the extracorporeal circuit and the dialyzate-side chamber is in fluid communication with the dialyzate circuit, and the apparatus has a preparation unit for online preparation of a solution. The apparatus has a first means for carrying out a priming mode and a second means for carrying out an initial treatment mode. The first means is configured to control the preparation unit to prepare a flushing solution having a pH of ≥7.3, with the extracorporeal circuit being filled with the flushing solution. The second means is configured to control the preparation unit to prepare the dialyzate having a pH of ≥7.3, with the dialyzate circuit being filled with the dialyzate.

18 Claims, 2 Drawing Sheets

(51) Int. Cl.
  *A61M 1/16* (2006.01)
  *A61M 1/34* (2006.01)
  *A61M 1/36* (2006.01)
  *F04B 43/00* (2006.01)
  *F17D 3/00* (2006.01)

(52) U.S. Cl.
  CPC ........ *A61M 1/3462* (2013.01); *A61M 1/3465* (2014.02); *A61M 1/365* (2014.02); *A61M 1/3643* (2013.01); *A61M 1/3644* (2014.02); *A61M 1/3649* (2014.02); *A61M 2205/3324* (2013.01)

(56) References Cited

FOREIGN PATENT DOCUMENTS

WO WO 2004/043520 5/2004
WO WO 2013/182287 12/2013

OTHER PUBLICATIONS

Amore et al. Use of alkaline rinsing solution to prevent hypersensitivity reactions during hemodialysis: data from a multicentre retrospective analysis. Journal of Nephrology, vol. 12, No. 6, Nov. 1, 1999, pp. 383-389.

Renaux et al. Activation of the kallikrein-kinin system in hemodialysis: Role of membrane electronegativity, blood dilution, and pH. Kidney International, vol. 55, No. 3, Mar. 1, 1999, pp. 1097-1103.

Coppo et al. Bradykinin and nitric oxide generation by dialysis membranes can be blunted by alkaline rinsing solutions. Kidney International, vol. 58, No. 2, Aug. 1, 2000, pp. 881-888.

* cited by examiner

BLOOD TREATMENT APPARATUS FOR REDUCING THE PROBABILITY OF CONTACT PHASE ACTIVATION

BACKGROUND OF THE INVENTION

1. Field of the Invention

The present invention relates to a blood treatment apparatus having at least one extracorporeal circuit and having at least one dialyzate circuit and having at least one dialyzer which has at least one blood-side chamber and at least one dialyzate-side chamber separated from the blood-side chamber by one or more membranes, wherein the blood-side chamber is in fluid communication with the extracorporeal circuit and the dialyzate-side chamber is in fluid communication with the dialyzate circuit. The blood treatment apparatus furthermore has a preparation unit for the online preparation of a solution.

2. Description of Related Art

Such blood treatment apparatus are known from the prior art, for example, in the form of hemodialysis devices. In these known devices, the preparation unit serves the online preparation of the dialyzate and optionally of the substituate. In this respect, the "online preparation" is to be understood such that the solution, i.e. the dialyzate or the substituate, for example, is prepared in the device itself and is not e.g. brought to the dialysis machine in containers or the like.

With various membrane surfaces of the dialyzer, a so-called contact phase activation can occur on the first contact of the blood of the treated patient. This contact phase activation is triggered, on the one hand, by the folding of proteins of the blood by a pH beneath the physiological level of 7.4 and, on the other hand, by binding points on the artificial surface such as by charges.

The influence of the pH of the blood on the biocompatibility of the total system is described, for example, in J. Renaux et al.: Activation of the kallikrein-kinin system in hemodialysis: Role of membrane electronegativity, blood dilution and pH (Kidney International, Vol. 55 (1999, p. 1097-1103) and in R. Coppo et al.: Importance of the bradykinin-nitric oxide synthase system in the hypersensitivity reactions of chronic hemodialysis patients (Nephrol Dial Transplant (2000) 15: 1288-1290).

SUMMARY OF THE INVENTION

It is the underlying object of the present invention to further develop a blood treatment apparatus of the initially named kind such that the probability for the occurrence of the contact phase activation is reduced with respect to known blood treatment apparatus.

This object is satisfied by a blood treatment apparatus having the features described herein.

Provision is made in this respect that the blood treatment apparatus has first means for carrying out a priming mode and second means for carrying out an initial treatment mode, wherein the first means are configured such that they control the preparation unit such that a flushing solution having a pH of ≥7.3, and preferably of ≥7.4, is prepared and such that the extracorporeal circuit is filled with this flushing solution. The second means are furthermore configured such that they control the preparation unit such that dialyzate having a pH of ≥7.3, and preferably of ≥7.4, is prepared and such that, in a first phase of the treatment, in a treatment mode, the dialyzate having the named pH flows through the dialyzer and/or is supplied to the extracorporeal blood circuit as a substituate. The blood treatment apparatus furthermore has at least one control or regulation unit which operates the first means before the second means so that the priming is carried out first and then the initial phase of the actual blood treatment is carried out.

It is thus the underlying idea of the invention to set a pH for the priming close to the physiological pH of blood and also to maintain the pH in accordance with the invention over a certain time during the initial phase of the treatment.

The pH of the dialyzate or substituate can be, but does not have to be, identical to the pH of the priming solution.

The composition of the dialyzate or of the substituate can only be adapted to the prescribed composition or concentration by third means after the completion of the initial phase.

The present invention makes use of the recognition that the pH is not only significant during the priming, but also in the initial phase of the blood treatment. During this initial phase, in which the pH is held in the range in accordance with the invention, the membrane of the dialyzer is coated with proteins and cells so that a free artificial surface is no longer present which can come into first contact with the proteins of the blood. The probability of the contact phase activation is thus minimized.

The membrane is preferably a plurality of hollow fiber membranes which are combined to a bundle in a housing.

It is admittedly known from the prior art to subject the extracorporeal circuit to a priming prior to the treatment; however it is not known in the prior art in this respect to set the pH in accordance with the invention and it is also not known to maintain the pH in accordance with the invention during the initial phase of the blood treatment. It is furthermore not usual practice to go beyond the physician's prescription particularly in this phase so that the procedure in accordance with the invention therefore represents a surprising teaching.

The historical prior art is priming using a saline solution. Since this solution does not contain any buffer, the pH of the blood is not changed in this case despite dilution. In particular with patients with pronounced metabolic acidosis, a triggering of contact phase activation can take place in this respect provided that the artificial membrane surfaces offer a sufficient number of binding points.

With known online HDF (hemodiafiltration) machines, the combination of the substitution solution, which is simultaneously also used as the dialyzate, is as a rule also used for priming. The disadvantage of this solution is that the pH is not independent of the setting for correcting metabolic acidosis during priming. It can thus be advisable on when starting dialysis of new patients to extend the correction of metabolic acidosis over several treatments and to work with a comparatively low bicarbonate solution at first. The consequence of this is a pH of the priming solution beneath the physiological range so that a contact phase activation can be the accompaniment.

The first, second and third means can be formed by one and the same component. In this case, there is thus only a difference between the means in the operating mode in which they are operated, i.e. the first means are operated in a first operating mode (during priming), the second means in a second operating mode (during the initial treatment phase) and the third means in a third operating mode (during the treatment phase after completion of the initial treatment phase). The preparation unit is operated in dependence on the operating mode of the means.

However, the case is also covered by the invention that all of the means, or at least two of the means, are formed by different components which are operated in the aforesaid modes.

The means can also be a program code which is configured such that it controls specific modules, e.g. the pumps, differently in different phases. This means that different values (quantities, concentrations) are stored for each phase in the program code which then result in different mixing ratios of the concentrates with the water.

The component or components can, for example, be a controller, calculator, processor, etc. which controls the preparation unit such that it prepares the desired solution in dependence on the operating mode of the means. The control or regulation unit sets the operating mode of the means, which results in a corresponding operation of the preparation unit. The means can represent an integral component of the control or regulation unit or can be configured as separate elements with respect to the control or regulation unit.

The first and second means can be configured such that they control the preparation unit in an identical manner, which has the consequence that the composition of the flushing solution for the priming and of the dialyzate are identical for the initial phase of the treatment.

In a further embodiment, the second means are configured such that they control the preparation unit such that the substitute is prepared with a pH of ≥7.3, and preferably of 7.4. Provision can be made in this respect that the second means are configured such that they control the preparation unit for the preparation of the dialyzate and of the substitute in an identical manner. This has the consequence that the compositions of the dialyzate and of the substitute are identical.

In a preferred embodiment, the compositions of the dialysate, of the substitute and of the flushing solution are at least identical up to the completion of the initial phase of the dialysis treatment.

Provision is made in a further embodiment of the invention that the second means are designed such that they are operated for a predefined time or for a duration which depends on at least on parameter. This predefined time can, for example, be a time period of up to 15 minutes. This value is, however, only an exemplary value.

The parameter can, for example, be the quantity of the plasma extracted via the membrane of the dialyzate or a parameter correlated therewith. It is thus conceivable, for example, to carry out the initial phase for so long until a defined quantity of extracted plasma is present.

It is also conceivable to use the ultrafiltration coefficient of the membrane as the parameter which decides on the duration of the initial phase to achieve an estimate of the design of a secondary membrane.

It is thus conceivable that the initial phase ends at the end of a fixed time and/or after obtaining a fixed quantity of plasma extracted over the membrane.

The first means are preferably configured such that the dialyzate-side chamber of the dialyzer in addition to the extracorporeal circuit, is also filled with flushing solution within the framework of the priming.

In a further embodiment of the invention, the blood treatment apparatus has third means for carrying out a treatment mode following the initial treatment mode, wherein the third means are configured such that they control the preparation unit such that the dialyzate and/or the substitute are matched in their composition to a prescribed composition or correspond thereto. The third means are operated after the second means by means of the control or regulation unit of the device. This means that the dialyzate and/or the substituate are matched to the prescribed composition or concentration subsequent to the initial phase, which can take place step-wise or also by means of a ramp or constantly.

In a preferred embodiment of the invention, the setting of the pH of the respective solution takes place by means of the bicarbonate concentration of the solution prepared in the preparation unit.

The preparation unit can thus have conveying means for conveying bicarbonate and in particular a concentrate containing bicarbonate, wherein the conveying means are configured such that the perform the setting of the pH by the conveying of bicarbonate.

A specific pH of the flushing solution of the dialyzate or of the substituate can thus be set via the quantity or concentration of bicarbonate.

In an embodiment of the invention, the preparation unit is designed such that the conveying of bicarbonate takes place in dependence on an acid concentration, e.g. on the acetate concentration or on the citrate concentration, of the solution prepared in the preparation unit. The acetate concentration can be known, e.g. from an internal data table, or can also be measured. The bicarbonate concentration is then set in dependence on the acetate concentration to obtain a specific pH of the solution.

Provision is made in a further embodiment of the invention that at least one conveying means, preferably a pump, is arranged in the dialyzate circuit for conveying dialyzate and that the control or regulation unit is configured such that the conveying means is reduced with respect to its conveying rate or is fully stopped when the second means are active, i.e. during the initial phase of the treatment.

An increase in the speed of the correction of metabolic acidosis can thus occur in the blood of the patient with otherwise unchanged parameters by the setting of the pH in accordance with the invention. The final level is not influenced.

This initial effect will in particular be the highest with the incident patients since there the difference between the bicarbonate concentration in the priming fluid or during the initial phase of the dialysis from the prescription of the dialyzate is the highest. The difference can amount to 5 to 7 mmol/l, for example. In order now to limit the mass transport of bicarbonate into the blood and thus to make the temporal increase in the pH in the blood slower, it is conceivable to limit the dialyzate flow in the initial phase of the treatment, i.e. that is while the second means are active, and to set it to a value of zero in an extreme case. A pure hemofiltration is carried out in the starting point in this case. Such a procedure is known from DE 10 2012 011 196 A1.

Provision is made in a further embodiment of the invention that the first or second or third means are configured such that the flushing solution or that the dialyzate or the substituate have a pH in the range between 7.3 and 7.7, preferably in the range between 7.35 and 7.7, and particularly preferably in the range between 7.35 and 7.45.

The preparation unit can have a main line which is connected to a water port, in particular for RO water. One or more concentration lines, which are in fluid communication with one or more concentrate reservoirs, can open into this main line. The concentrate, such as an acid concentrate and a base concentrate, can be conveyed from these reservoirs into the main line by pumps in order to prepare the finished solution (flushing solution, dialyzate or substitution solution) in this manner.

BRIEF DESCRIPTION OF THE DRAWINGS

Further details and advantages of the invention will be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In a preferred embodiment of the invention, the embodiment relates to a hemodialysis device having an extracorporeal blood circuit whose lines are connected or can be connected to the patient via a venous port and via an arterial port. These lines are connected to a dialyzer which is divided by a plurality of hollow fibers into blood-side chambers and into a dialyzate-side chamber. The dialyzate-side chamber surrounds the hollow fibers and is connected to or forms a part of the dialyzate circuit.

The dialyzate circuit has a feed line to the dialyzer which is connected to the preparation unit and has a drain line which leads to the drain for the consumed dialyzate. A dialyzate pump is located in this drain line. The blood pump is preferably located in the blood circuit upstream of the dialyzer in the direction of flow of the blood.

A substituate solution can furthermore be provided which opens from the preparation unit into the extracorporeal circuit, and indeed before and/or after the dialyzer, so that a predilution or postdilution is possible.

The preparation unit has a main line which is connected to a source for RO water. Concentrate lines are furthermore provided through which the acid concentrate, on the one hand, and the base concentrate, on the other hand, are conveyed into the main line by means of corresponding conveying pumps. The correct composition of the solution prepared in this manner can be determined via one or more conductivity measurement cells.

The solution prepared in the preparation unit is used as a flushing solution, as a dialyzate and as a substituate.

Figure 1:
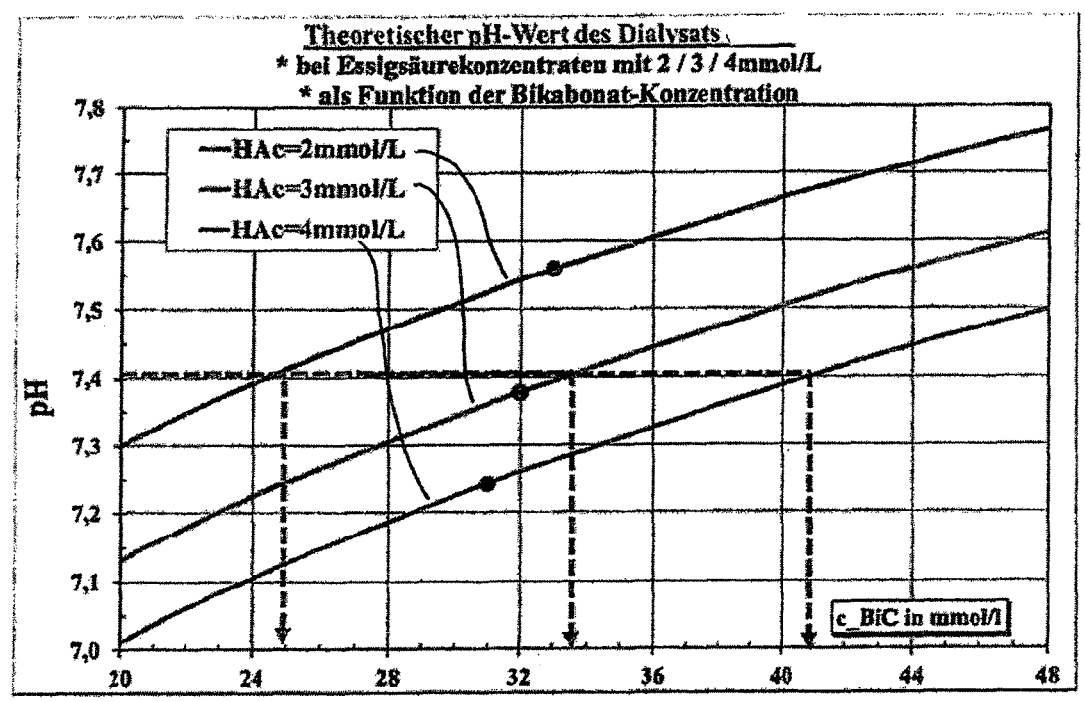
FIG. 1: the dependency of the pH of the solution on the bicarbonate concentration and on the acetic acid concentration or acetate concentration.
Figure 2:
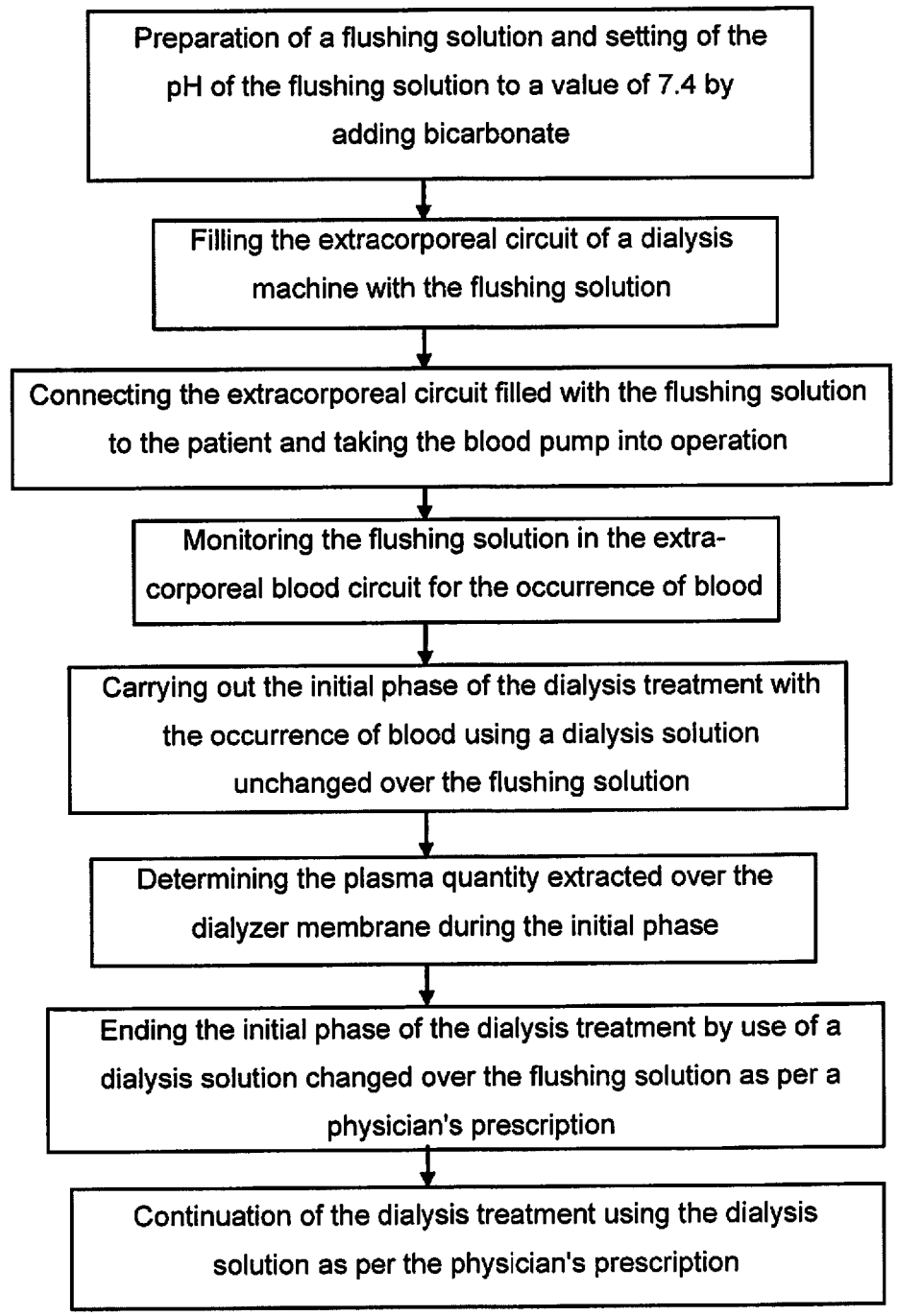
FIG. 2: an exemplary flowchart for operating a blood treatment apparatus in accordance with the invention.

FIG. 2 shows an exemplary flowchart for the operation of a blood treatment apparatus in accordance with the invention.

The priming of the extracorporeal circuit with the flushing solution takes place before the actual blood treatment. In this respect, the composition of the priming solution is controlled such that on the connection of the blood circuit, both the dialyzate-side chamber and the total extracorporeal circuit is filled with a solution or with the flushing solution which has a pH of ≥7.4.

To reach this goal, the preparation unit of the blood treatment apparatus meters in bicarbonate in dependence on the acetate concentration corresponding to an internal data table. The only Figure shows the corresponding correlation.

Different acetate concentrations or acetic acid concentrations of 2, 3 and 4 mmol/l are shown in this Figure. The pH is entered on the ordinate and the bicarbonate concentration is entered on the abscissa which has to be set correspondingly differently in dependence on the acetate concentration to obtain the desired pH of 7.4. A bicarbonate concentration of approximately 25 mmol/l is thus required with an acetic acid concentration of 2 mmol/l, a bicarbonate concentration of approximately 33.5 mmol/l with an acetic acid concentration of 3 mmol/l, and a bicarbonate concentration of approximately 41 mmol/l with an acetic acid concentration of 4 mmol/, to obtain the desired pH of 7.4.

After the priming, the extracorporeal circuit filled with the flushing solution is connected to the patient, i.e. to the venous port and to the arterial port.

The blood pump is subsequently taken into operation.

On the detection of blood in the venous limb of the hose system of the extracorporeal circuit, the composition of the priming solution for the dialyzate or for the substituate is first taken over, i.e. not changed. The dialysis is now run in for so long with a dialyzate having a physiological pH in this initial phase until a completion of the protein charging of the membrane can be assumed. As stated above, this can be the case either after a fixed time and/or after obtaining a fixed quantity of plasma extracted over the membrane. The development of the ultrafiltration coefficient of the membrane can also be used as the criterion for the completion of the initial phase of the treatment to obtain an estimate of the setup of a secondary membrane. A table can be provided in which corresponding completion criteria for different filter types can be stored.

The composition of the priming solution for the substituate can also be maintained in the pH range ≥7.3 or ≥7.4 or not be changed.

If such a secondary membrane is reached, the probability for the occurrence of the contact phase activation is minimized.

After completion of this initial phase, the bicarbonate concentration of the dialyzate and of the substituate are matched, i.e. lowered, to the prescribed concentration via a ramp function so that smaller pH values are produced than during the priming and the initial phase.

As stated above, the dialyzate pump can be operated at a rate reduced with respect to normal operation or can be fully stopped during the initial phase of the treatment. This has the advantage that the mass transfer of bicarbonate into the blood is limited and thus the speed of the correction of metabolic acidosis is reduced.

The present invention relates to the blood treatment apparatus in accordance with the invention and also to a method of carrying out a blood treatment by means of the blood treatment apparatus.

In accordance with the method, a flushing solution having a pH of ≥7.3, and preferably of ≥7.4, is first filled into the extracorporeal circuit and additionally optionally into the dialyzate-side chamber and the treatment is subsequently likewise carried out subsequent to the priming using a dialyzate having a pH of ≥7.3, and preferably of ≥7.4. This initial phase of the dialysis treatment can be carried out for a specific length of time or for so long until a specific quantity of blood is flowed through the membrane.

The method can be carried out in accordance with every single aspect of one of the claims.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A blood treatment apparatus comprising:
   an extracorporeal circuit and a dialyzate circuit with a dialyzer having a blood-side chamber and a dialyzate-side chamber, which is separated from the blood-side chamber by a dialyzer membrane, the blood-side chamber being in fluid communication with the extracorporeal circuit and the dialyzate chamber being in fluid communication with the dialyzate circuit,
   a preparation unit for online preparation of a solution,
   a first means for carrying out a priming mode, and a second means for carrying out an initial treatment mode,
   the first means being programmed to control the preparation unit such that a flushing solution having a pH of >7.3 is prepared, and such that the extracorporeal circuit is filled with the flushing solution, and the second means being programmed to control the preparation unit such that a dialyzate having a pH of >7.3 is prepared, and such that the dialyzate circuit is filled with the dialyzate,
   a control or regulation unit which operates the first means before the second means,
   the preparation unit including a means for conveying bicarbonate, with the bicarbonate conveying means being configured to carry out a setting of the pH by conveying the bicarbonate, and
   a third means for carrying out a treatment mode following the initial treatment mode, the third means being programmed to control the preparation unit such that a composition of the dialyzate is matched to a prescribed composition, with the control or regulation unit being configured such that the third means is operated after the second means.

2. The blood treatment apparatus in accordance with claim 1, wherein the first means and the second means are configured programmed to control the preparation unit in an identical manner such that a composition of the flushing solution and the composition of the dialyzate are identical in the initial treatment mode.

3. The blood treatment apparatus in accordance with claim 1, wherein the second means is programmed to control the preparation unit such that a substituate having a pH of ≥7.3 is prepared, with the second means being programmed to control the preparation unit for preparing the dialyzate and the substituate in an identical manner so that the compositions of the dialyzate and of the substituate are identical.

4. The blood treatment apparatus in accordance with claim 1, wherein the second means is programmed to be operated for a predetermined time or for a duration which depends on at least one parameter.

5. The blood treatment apparatus in accordance with claim 4, wherein the at least one parameter is a quantity of plasma extracted over the dialyzer membrane, or a parameter correlated therewith, or an ultrafiltration coefficient of the dialyzer membrane.

6. The blood treatment apparatus in accordance with claim 1, wherein the first means is programmed such that the dialyzate-side chamber is also filled with flushing solution in addition to the extracorporeal circuit.

7. The blood treatment apparatus in accordance with claim 1, wherein the third means is programmed to control the preparation unit such that the dialyzate and/or the substituate are matched in their composition to a prescribed composition.

8. The blood treatment apparatus in accordance with claim 1, wherein the preparation unit is configured such that the conveying of the bicarbonate takes place in dependence on an acetate concentration or a citrate concentration of the solution prepared in the preparation unit.

9. The blood treatment apparatus in accordance with claim 1, further comprising a conveying means arranged in the dialyzate circuit for conveying the dialysate, with the control or regulation unit being configured such that the dialyzate conveying means is reduced with respect to a conveying rate thereof, or is stopped, when the second means is active.

10. The blood treatment apparatus in accordance with claim 3, wherein the apparatus is configured such that the flushing solution or the dialyzate or the substituate has a pH in a range between 7.3 and 7.7.

11. The blood treatment apparatus in accordance with claim 1, wherein the preparation unit has a main line which is connected to a water port, and wherein one or more concentrate lines which are in fluid communication with one or more concentrate reservoirs open into the main line.

12. The blood treatment apparatus according to claim 1, wherein the flushing solution has a pH of ≥7.4.

13. The blood treatment apparatus according to claim 1, wherein the dialyzate has a pH of ≥7.4.

14. The blood treatment apparatus according to claim 1, wherein the bicarbonate is a concentrate containing bicarbonate.

15. The blood treatment apparatus according to claim 3, wherein the substituate has a pH of ≥7.4.

16. The blood treatment apparatus according to claim 10, wherein the flushing solution or the dialyzate or the substituate has a pH in a range between 7.35 and 7.7.

17. The blood treatment apparatus according to claim 10, wherein the flushing solution or the dialyzate or the substituate has a pH in a range between 7.35 and 7.45.

18. The blood treatment apparatus according to claim 11, wherein the water port is a reverse osmosis water port.

* * * * *